(12) United States Patent
Gordon et al.

(10) Patent No.: US 6,579,321 B1
(45) Date of Patent: Jun. 17, 2003

(54) INTERVERTEBRAL DISC REPLACEMENT PROSTHESIS

(75) Inventors: Jeffrey D. Gordon, Nashville, TN (US); John M. Dawson, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 09/572,057

(22) Filed: May 17, 2000

Related U.S. Application Data

(60) Provisional application No. 60/134,500, filed on May 17, 1999.

(51) Int. Cl.[7] ............................................. A61F 2/44
(52) U.S. Cl. ................................... 623/17.16; 623/17.11
(58) Field of Search ............................ 623/17.11–17.16

(56) References Cited

U.S. PATENT DOCUMENTS

| | | | | |
|---|---|---|---|---|
| 5,895,428 A | * | 4/1999 | Berry | 623/17.15 |
| 6,117,174 A | * | 9/2000 | Nolan | 606/61 |
| 6,136,031 A | * | 10/2000 | Middleton | 623/17.16 |
| 6,146,421 A | * | 11/2000 | Gordon et al. | 623/17.15 |
| 6,395,035 B2 | * | 5/2002 | Bresina et al. | 623/17.15 |

OTHER PUBLICATIONS

"Biomechanics—BAK ™ Interbody Fusion System" brochure, SulzerMedica, Sulzer Spine Tech, 1998.
"Patient Guide—BAK ™ Interbody Fusion System" brochure SulzerMedica, Sulzer Spine Tech, 1999.
"Intervertebral Disc Replacement, Experimental Study", Kostuik, Clinical Orthopedics and Related Research No. 337, pp. 27–41, 1997.
Manufacturer Directory, ArtificialDisc.com, 2000.
Ray Threaded Fusion Cage ™ informational brochure, Surgical Dynamics.

* cited by examiner

*Primary Examiner*—Corrine McDermott
*Assistant Examiner*—Thomas C. Barrett
(74) *Attorney, Agent, or Firm*—Stites & Harbison PLLC; Richard S. Myers, Jr.

(57) ABSTRACT

An implantable intervertebral disc prosthesis that comprises a disc member having an upper surface, a lower surface, and a perimeter surface. The disc includes an axis at least one slit defined in the perimeter surface; the slit being of sufficient depth and thickness to provide flexure. The slit terminates in a perimeter opening larger than the slit thickness. The perimeter opening (i.e., hole) acts as a pivot point and relieves stress. The disc prosthesis optionally comprises a cavity with an upper seat defined on the lower surface, a lower disc having an upper and lower surface and a lower seat defined on the upper surface, and a support ball. The support ball engages the seat on the upper disc and the seat on the lower disc.

31 Claims, 5 Drawing Sheets

INTERVERTEBRAL DISC REPLACEMENT PROSTHESIS

This application claims priority to Provisional Application Serial No. 60/134,500, filed May 17, 1999, the contents of which are incorporated herein by reference.

BACKGROUND OF THE INVENTION

1. Field of the Invention

The human spine is a flexible structure comprised of thirty-three vertebrae. Intervertebral discs separate and cushion adjacent vertebrae. The intervertebral discs act as shock absorbers and allow bending between the vertebrae.

This invention relates to an intervertebral disc prosthesis that allows improved movement and range of motion for the recipient. The intention of this invention is to replace the disc with a device that mimics the geometrical and mechanical characteristics of a normal human intervertebral disc. The invention is a flexure system that acts as a spring. When acted on by any force or movement, the prosthesis of the present invention will react similarly to the reaction of a normal human intervertebral disc.

2. Description of Related Art

There have been devices developed and tested in the past in attempts to design a successful disc replacement. Problems with the development of a successful device include the difficulty in maintaining safety to the spinal cord and its nerve roots and that of the supporting body and head in a variety of postures during normal movement of the arms, legs, and torso.

For example, U.S. Pat. No. 5,827,328 to Butterman discloses an intervertebral prosthetic device that includes a compressible member with at least one spring that is pre-loaded to place the annulus fibrosis under tension and to reproduce the mechanical properties of a natural disc.

U.S. Pat. No. 5,320,644 to Baumgarter discloses a intervertebral disc prosthesis, but fails to disclose, among other things, a disc prosthesis with perimeter openings and a support ball. U.S. Pat. No. 5,895,428 to Berry discloses an implant that has an upper member that pivots and is locked into a lower member. Additionally, U.S. Pat. Nos. 5,556,431; 5,782,832; 5,888,226; 5,865,846; 5,888,223; 5,676,702; 4,932,975; and 5,423,817 generally relate to the area of disc replacement.

BRIEF SUMMARY OF THE INVENTION

Many spine operations involve problems with the intervertebral disc. The goal of spinal surgery is fusion, which is affected by biomedical factors including the load carried by a spinal fixation device and the flexibility of the spine-implant. It has been demonstrated that a boimechanically strong and clinically safe device restores sagittal alignment and stability. Restoration of the load carrying function of the spine is best accomplished by positioning the implant in the middle column of the spine. See Dawson et al., The Spinal Nail: A new implant for Short Segment Anterior Instrumentation of the Thoracolumbar Spine, Spine, 9(4), 1996; the contents of which are incorporated herein by reference.

Further, the designs of most spinal instrumentation systems are predicated upon eliminating motion at the affected levels. See Gurwitz et al., Biomechanical Analysis of Three Surgical Approaches for Lumbar Burst Fractures Using Short Segment Instrumentation, Spine 18:977–982, 1993.

A prior accepted remedy for disc resection has been disc fusion of the vertebra immediately superior to the resected disc space with the vertebra immediately inferior to the resected disc space. While in the past such fusion has had satisfactory results, such results are mixed. For example, the discs adjacent to the fusion site have a greater tendency to fail. This failure is believed by some to be caused by altered stress from altered spine kinematics. An additional reason for the additional disc failure may be the demands on the fusion device.

The disc prosthesis of the present invention has the objective of providing a vertebral disc prosthesis that will perform effectively and efficiently within a patient's spine over a long period of time, and that will not encourage degeneration of or cause damage to adjacent vertebrae. Further, it is flexible and permits limited motion rather than rigidly constraining its spinal level.

With regard to motion, the disc prosthesis of the present invention permits flexion-extension and lateral bending. These motions are achieved by deformation of the implant rather than articulation between parts as with other implants. Deformation occurs in the flexure system with each slit or slot behaving like a hinge.

The disc prosthesis of the present invention generally is an excellent implantable intervertebral disc prosthesis that comprises a disc member having an upper surface, a lower surface, and a perimeter surface. The disc includes an axis at least one slit defined in the perimeter surface; the slit being of sufficient depth and thickness to provide flexure. The slit terminates in a perimeter opening larger than the slit thickness.

Preferably the disc prosthesis of the current invention is shaped to fit between two vertebrae, and thus may have convex or flat upper or lower surfaces, as well as other appropriate shapes (i.e., oval or kidney shaped). Additionally, the vertebrae may be shaped to better receive the prosthesis of the present invention and thereby provide a more snug fit.

The perimeter opening (i.e., hole) acts as a pivot point and relieves stress. The hole may be circular or non-circular, centered or non-centered on the slit. Preferably, the hole is circular.

In another embodiment of the present invention, the replacement prosthesis, comprises an upper disc having an upper and lower surface and an upper seat defined on the lower surface, a lower disc having an upper and lower surface and a lower seat defined on the upper surface, and a support ball. The support ball engages the seat on the upper disc and the seat on the lower disc when the upper and lower discs are attached to one another and ready for insertion into the spine.

As stated above, the disc prosthesis of the present invention permits flexion-extension and lateral bending for a recipient of the disc by deformation of the disc. Preferably, the disc prosthesis of the present invention comprises a cavity through part of the axis of the disc, with the cavity housing a support ball. The support ball transfers the axial compression load and thereby decreases the deformation caused by axial compression. Additionally, loads that induce flexion-extension or lateral bending of the spine are also major components of spinal loading. Off-center compressive loads will cause the disc of the present invention to flex. With regard to flexion-extension, such loads will close a slit in hinge-like fashion and at the same time push against the support ball. An opposite slit will open because it rotates on the support ball. Because at least two opposite "hinges" are involved, the angle through which the disc prosthesis of the present invention is increased. Preferably, the angle is doubled. Additionally, the support ball maintains disc prosthesis height. If the prosthesis flattens any, pinching of the nerves may occur which could cause the recipient substantial pain. The support ball is preferably ceramic.

DETAILED DESCRIPTION OF THE INVENTION

As stated above, the disc prosthesis of the present invention is an implantable intervertebral disc prosthesis that comprises a disc member having an upper surface, a lower surface, and a perimeter surface. The disc includes an axis at least one slit defined in the perimeter surface; the slit being of sufficient depth and thickness to provide flexure. The slit terminates in a perimeter opening larger than the slit thickness. The prosthesis of the present invention assists in preserving normal ranges of movement.

The prosthesis of the present invention can be made to fit the cavity left by the removed disc and, when properly in place, provides a stress environment at the prosthesis/bone interface similar to normal in vivo conditions. Additionally, the vertebrae may be cut to provide a better, more secure fit for the disc prosthesis of the present invention.

In general, the shape of the disc prosthesis may be varied in the sagittal, frontal, and coronal plane to match the natural disc being replaced. For example, the implant may be round, oval, or kidney-shaped in the coronal plane. The upper and lower surfaces of the implant may be parallel (i.e., the disc may have a flat top and bottom surface), or they and the perimeter surface may be convex or angled to match the shape of the natural disc.

The disc prosthesis of the present invention may be made of any surgically implantable metal or composite that allows the disc to carry out the proper functions of the invention (i.e., provide support and flexibility in place of the removed natural disc). Thus, fatigue strength of the materials used in the present invention is of utmost importance. Preferably, the disc prosthesis of the present invention is made of stainless steel, a composite material, cobalt chrome, titanium, or a combination thereof.

Figure 1:
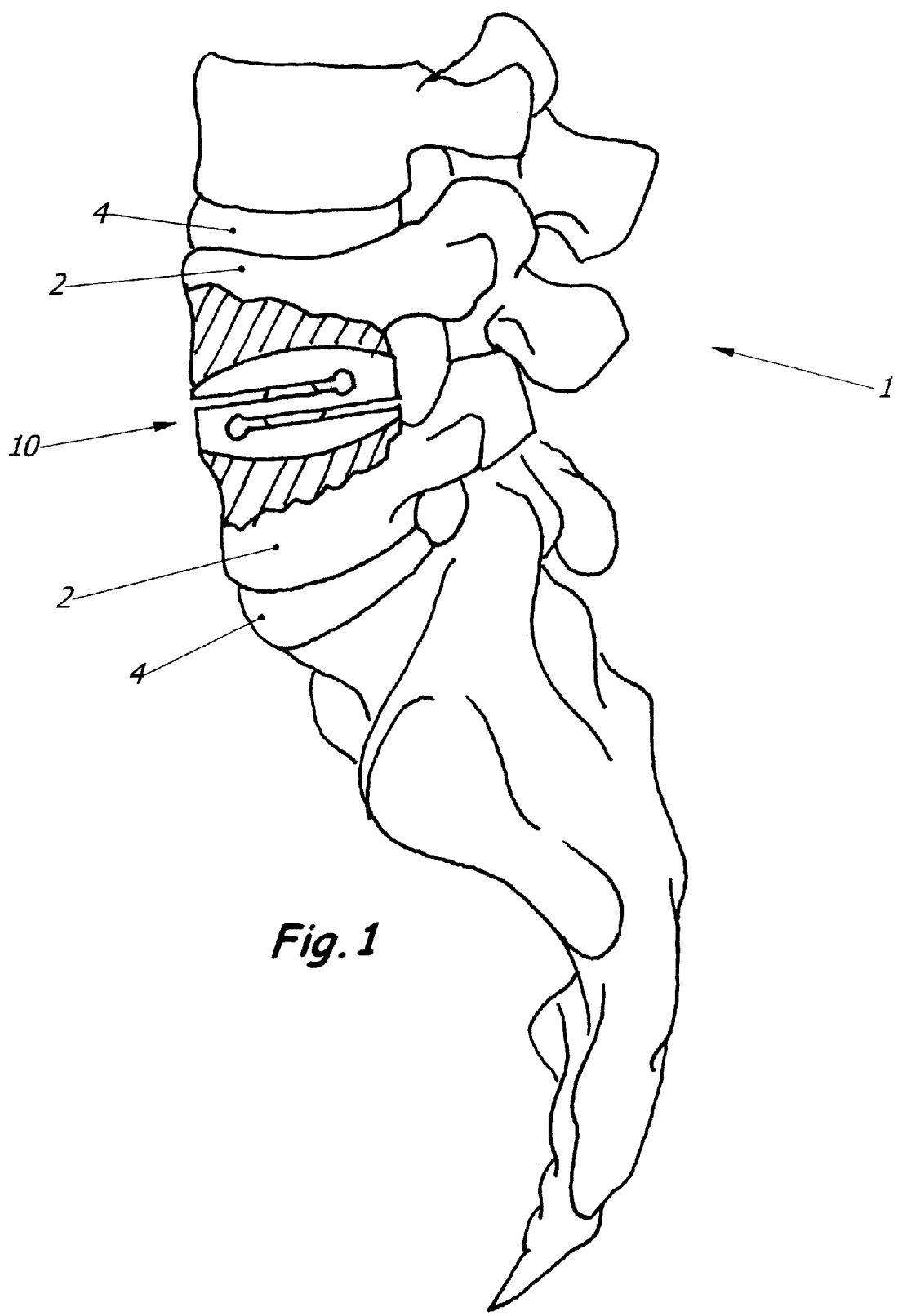
FIG. 1 depicts the disc prosthesis of the present invention inserted into the spine of a human. The disc prosthesis is positioned between two vertebrae.

As can be seen in FIG. 1, the disc prosthesis 10 is inserted into the spine 1 of a human. The disc prosthesis 10 is flanked by two vertebrae 2. In FIG. 1, the shaded portion if the vertebrae 2 is part of a cut-away view. The prosthesis disc 10 replaces the natural discs 4.

Figure 2:
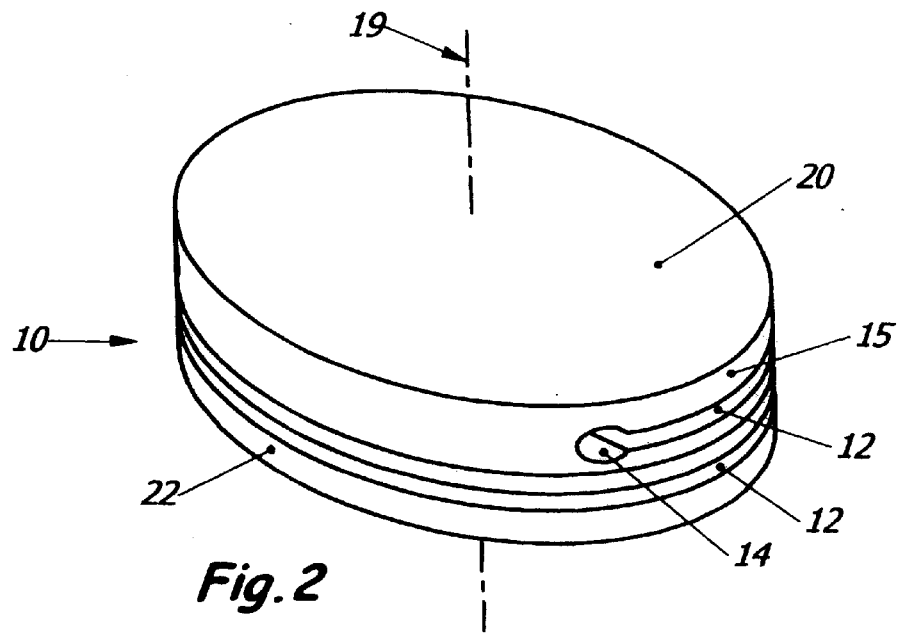
FIG. 2 depicts an embodiment of the disc prosthesis of the present invention. In this embodiment, the upper and lower surfaces are flat.

FIG. 2 depicts an embodiment of the disc prosthesis of the present invention. This embodiment comprises slits 12 defined in the perimeter surface 15 to assist the disc to achieve deformation. In this embodiment, the slits 12 terminate in perimeter openings 14, which are larger than the slit thickness. The dimension of the slits 12 (both their placement and their anterior-posterior depths and thickness) may be varied. Varying the sits in dimension or number changes the flexibility if the disc prosthesis 10 of the present invention.

In the embodiment depicted by FIG. 2, the slits 12 are substantially at a right angle to the axis of the disc member 10. In other embodiments a slit may be defined on the perimeter surface 15 transverse to the axis. However, since the upper and lower surfaces of a disc prosthesis do not have to be parallel, the slits do not have to be parallel with respect to the upper and lower surfaces or with respect to other slits. The number, thickness and depth of the slits may be varied to achieve the level of flexibility desired for the disc prosthesis. Thicker, deeper, or a greater number of slits will result flexibility.

Also in the embodiment shown by FIG. 2, the upper surface and the lower surface are depicted as being substantially flat. Of course, as stated above, there are many surface types within the scope of the present invention. Preferably, the disc prosthesis of the present invention comprise a coating on at least one surface to promote bone fixation. This coating may includes ceramic beads, wire meshes, and other types of ceramics.

As stated above, the slits used on the disc prosthesis terminate at perimeter openings 14, or holes. The dimensions of the perimeter openings may be varied to reduce stress and to change the flexibility of the prosthesis. The geometry of the perimeter openings can be circular or non-circular. Preferably, the perimeter openings are circular.

Figure 3:
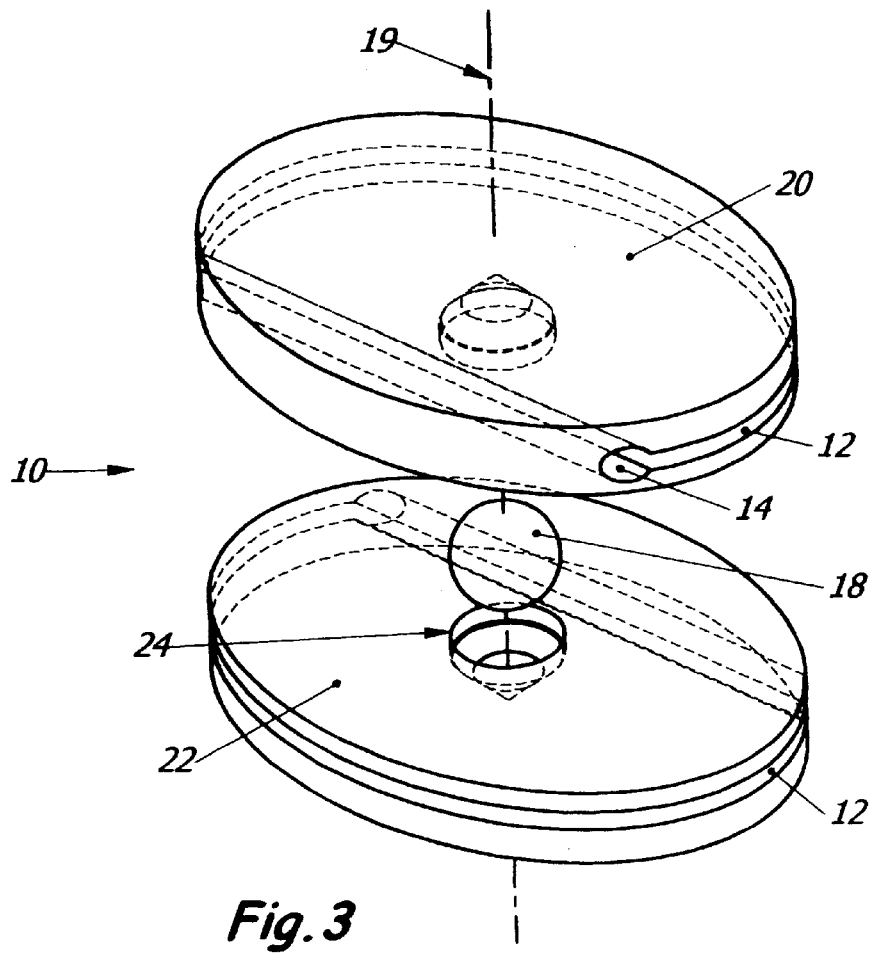
FIG. 3 depicts an exploded view of FIG. 2. In this embodiment, the disc prosthesis of the present invention comprises a support ball.

In FIG. 3, and other embodiments of the present invention wherein the disc prosthesis 10 comprises a support ball 18, the support ball 18 plays two roles with respect to load bearing. Because axial loading is a major component of spinal load, the implant 10 must be capable of withstanding substantial compression. Compression forces can range from one body weight to many body weights, depending on the particular activity. As stated above, through axial compression, load is transferred through the support ball 18 and as a result, deformation of the implant is reduced. The support ball 18 helps maintain the height of the disc.

The support ball 18 of the present invention may be made of any material that would assist in the load bearing functions of the disc. Preferred support balls of the present invention are made from cobalt chrome and ceramic. A more preferred support ball 18 is ceramic. Ceramics are very stiff, hard, and strong with respect to compression. The support ball acts as a transferor of compression load. The support ball is preferably substantially spherical. Most preferably, the support ball 18 is spherical. The support ball 18 is housed in a cavity 24 along the axis 19 of the disc prosthesis. In FIG. 3, a center axis 19 is shown, although any axis may be used that allows flexing action. In the embodiment of FIG. 3, the support ball 18 is housed in a single cavity 24 that is formed by a first disc member 20 and a second disc member 22. Typically, the first disc member has an upper seat defined on its lower surface and second disc member has a lower seat on its upper surface. Alternatively, the disc member has a cavity, and has an upper seat and a lower seat defined thereon and communicated with the cavity. The support ball is received by the cavity and engages the upper and lower seats so that compression forces are transformed from the upper seat to the lower seat. In other embodiments, the support ball may engage a first disc member with an upper seat and a lower disc member. The seats will be discussed more specifically below.

He Returning to the first disc member and the second disc member depicted in FIG. 3, the method of attaching the first disc member to the second disc member are not known to be critical as long as the resulting disc prosthesis is compatible with the objects of the present invention. While one member may be attached to the other using welding procedures, pins, screws may optionally be used to pack.

Loads that induce flexion-extension of lateral bending of the spine are also major components of spinal loading. Off center compressive loads cause the disc to flex. In flexion-extension, such loads will close one hinge and at the same time push against the support ball. That causes the opposite hinge to open in consequence because it rotates on the support ball.

Figure 4:
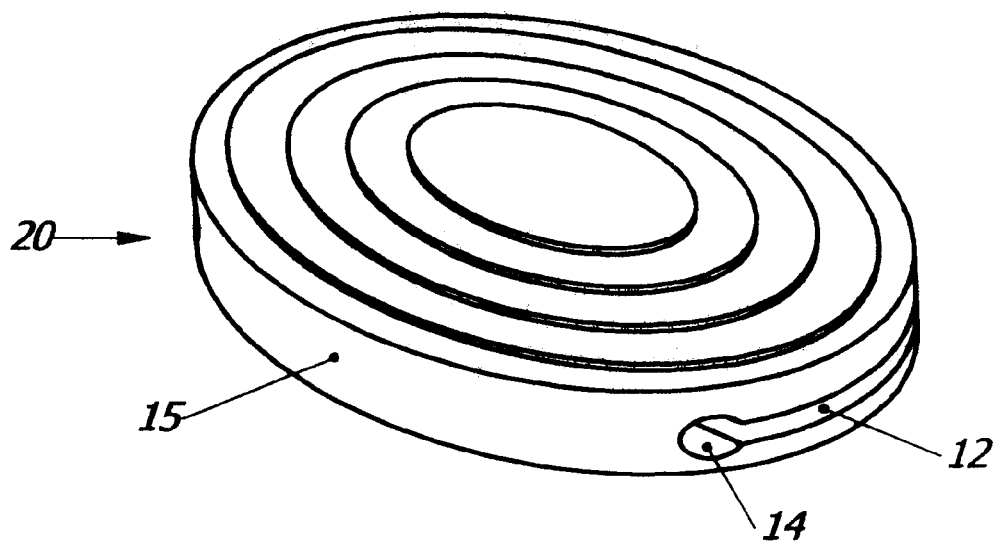
FIG. 4 depicts an embodiment of the present invention wherein the disc prosthesis has a cascading or stepped, convex surface.
Figure 5:
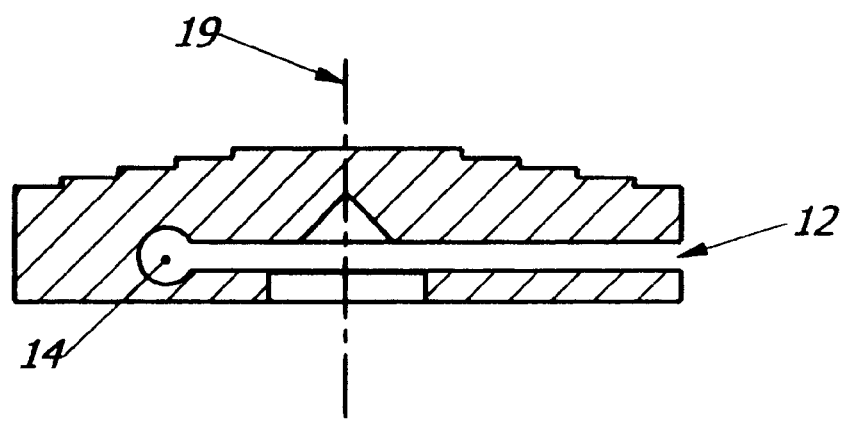
FIG. 5 is a profile view of an embodiment where the disc prosthesis forms a seat to receive a support ball.

FIG. 4 illustrates a first disc member or an upper disc that is convex on the top surface. More specifically, the convex nature was achieved ridges or steps. FIG. 5 illustrates a profile view if a disc member or an upper disc that is convex on the bottom surface. In this view, the slit 12 is seen terminating into the perimeter opening 14. The cavity 24 and lower seat 26 for receiving the support ball (not shown in this figure) are defined in this embodiment about the axis 19.

Figure 6:
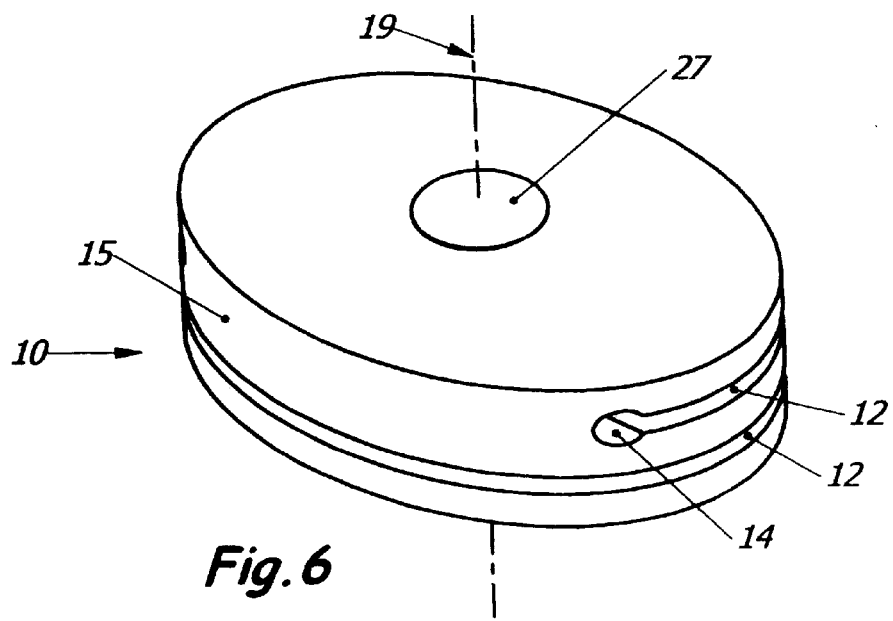
FIG. 6 depicts an embodiment of the present invention where the disc is one piece with a cavity for the support ball. The support ball is held within the cavity with bearing tops.
Figure 7:
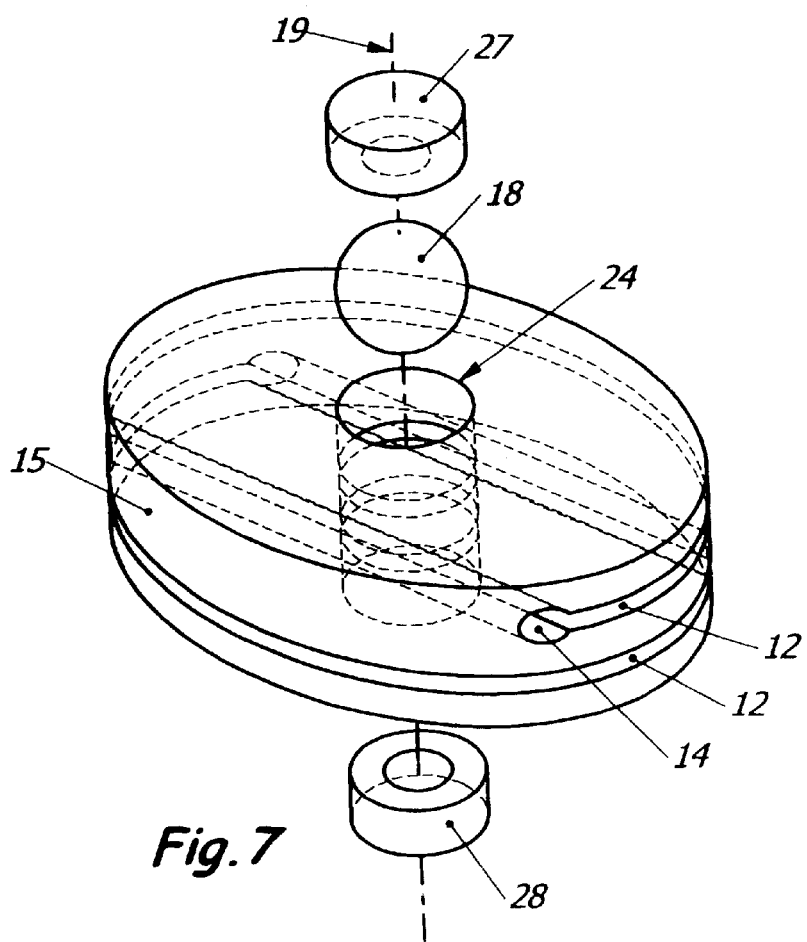
FIG. 7 is an exploded view of the disc of FIG. 6.

FIGS. 6 and 7 (exploded view of FIG. 6) are representative of an embodiment of the present invention where a cavity 24 for receiving the support ball 18 is defined in the disc member 10 about the axis 19. The support ball 18 is housed in the cavity 24 by an upper bearing cap 27 and a lower bearing cap 28. The bearing caps optionally may seal the cavity in the same manner that an upper disc is connected to a lower disc. That is, the bearing caps may be sealed by welding, screws, pins, or by screwing into the disc member.

Figure 8:
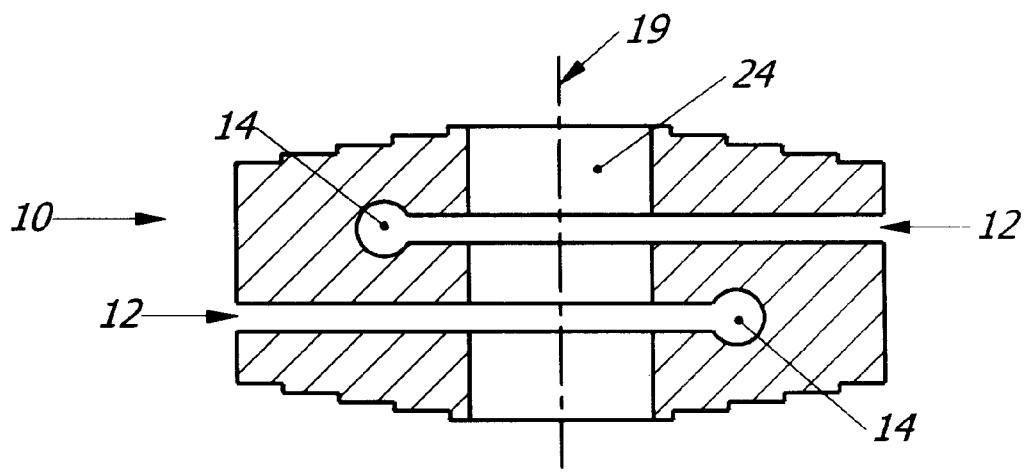
FIG. 8 is a profile cut-away view of a disc member of the present invention with a cavity to receive a support ball.

FIG. 8 shows a profile of the embodiment discussed in FIGS. 6 and 7, above. In this view the slits 12 are aligned on opposite sides of the axis 19. The slits may be arranged in a similar fashion when the prosthesis comprises an upper disc and a lower disc.

Figure 9:
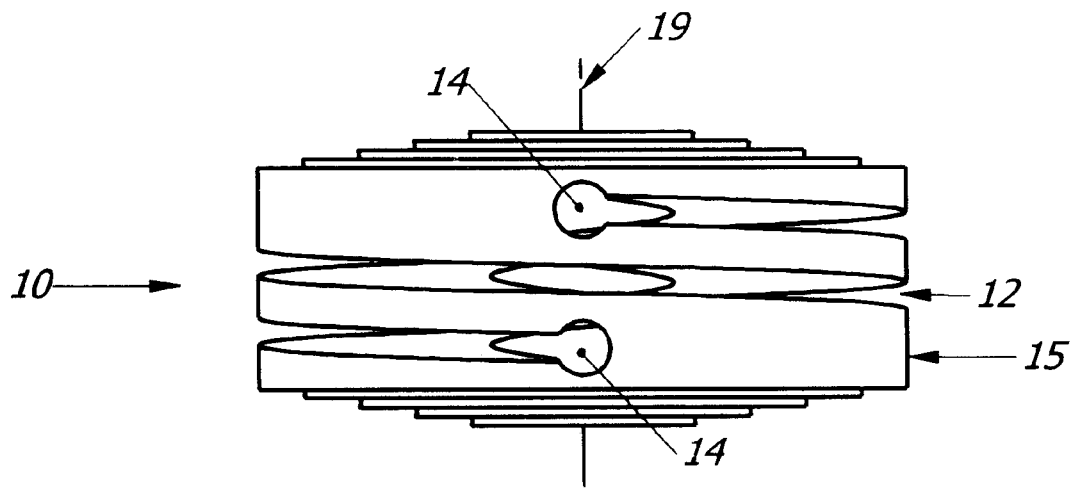
FIG. 9 is a profile view of the disc prosthesis of the present invention wherein a slit is helical to the axis of the disc member.

Finally, FIG. 9 offers a view of an embodiment of the disc prosthesis 10 of the present invention comprising one slit 12 along the perimeter surface 15 that terminates into two perimeter openings 14. In this embodiment, the slit 12 is defined in a helical manner about the perimeter surface 15. That is, the slit 12 is helical to the axis (not shown in this drawing).

Immediate and long term fixation of the disc prosthesis of the present invention may be accomplished by incorporating any number of design features that are typical for orthopedic devices. For example, the upper and lower surfaces may be flat to match cuts made by the surgeon or may be domed-shaped (i.e., have at least one convex surface) to fit the natural geometry of the vertebral bodies above and/or below the implant. Additionally, as stated above, the vertebral bodies may be modified to better receive and hold the prosthesis discs.

The upper and lower surfaces of the prosthesis of the present invention may incorporate blunt or sharp, short or tall pegs. Further, flanges may be added for screw fixation into the adjacent and subjacent vertebral bodies. In addition to being optionally held by screw fixation, other known methods may be used to help secure the disc prosthesis of the present invention between two vertebrae.

The upper and lower surfaces may be smooth or may have stepped, convex contours. The contours may be in a concentric, radial, or grid pattern and may or may not be sharp. Additionally, the upper and lower surfaces may be polished, sandblasted, ceramic coated, or covered with sintered beads or mesh.

The disc prosthesis of the present invention may be inserted into the spine using standard medical procedures. For example, see Benzel, Spine Surgery: Techniques, Complication Avoidance, and Management, 1999, the contents of which are incorporated herein by reference. Particularly see Benzel at Section 11, pages 143–192.

All cited patents and publications referred to in this application are herein expressly incorporated by reference.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the following claims.

We claim:

1. An implantable intervertebral disc replacement prosthesis, comprising:

a disc member having an upper surface, a lower surface, and a perimeter surface, and having an axis, the disc member having a slit defined in the perimeter surface to provide flexibility to the disc member, the slit having a slit thickness and a first end and a second end, with each end terminating in a perimeter opening larger than the slit thickness, a cavity along the axis of the disc, and a support ball housed in the cavity.

2. The implantable intervertebral disc replacement prosthesis of claim 1, wherein the slit is transverse to the axis of the disc member.

3. The implantable intervertebral disc replacement prosthesis of claim 2, wherein the slit is substantially at a right angle to the axis of the disc member.

4. The implantable intervertebral disc replacement prosthesis of claim 1, wherein at least one of the upper surface or the lower surface is convex.

5. The implantable intervertebral disc replacement prosthesis of claim 1, wherein at least one of the upper surface or the lower surface is substantially flat.

6. The implantable intervertebral disc replacement prosthesis of claim 1, wherein the prosthesis is shaped to fit a cavity between two vertebrae.

7. The implantable intervertebral disc replacement prosthesis of claim 1, wherein the prosthesis is kidney-shaped.

8. The implantable intervertebral disc replacement prosthesis of claim 1, wherein the perimeter opening is circular-shaped.

9. The implantable intervertebral disc replacement prosthesis of claim 1, wherein the perimeter opening is non-circular-shaped.

10. The implantable intervertebral disc replacement prosthesis of claim 1, wherein the disc permits flexion-extension and lateral bending for a wearer of the prosthesis by deformation of the disc.

11. The implantable intervertebral disc replacement prosthesis of claim 1, wherein the prosthesis is a surgically implantable metal or composite.

12. The implantable intervertebral disc replacement prosthesis of claim 1, wherein said prosthesis is titanium.

13. The implantable intervertebral disc replacement prosthesis of claim 1, wherein said prosthesis is stainless steel, a composite material, or cobalt chrome.

14. The implantable intervertebral disc replacement of claim 1, wherein the axis is a center axis.

15. The implantable intervertebral disc replacement prosthesis of claim 1, wherein the ball is ceramic.

16. The implantable intervertebral disc replacement prosthesis of claim 1, whereby the support ball acts as a transferor of compression load.

17. The implantable intervertebral disc replacement prosthesis of claim 1, wherein:

the disc member has a cavity defined therein;

the disc member has an upper seat and a lower seat defined thereon and communicated with the cavity;

the prosthesis further includes a support ball received in the cavity and engaging the upper and lower seats so that compression forces are transferred from the upper seat through the support ball to the lower seat.

18. The implantable intervertebral disc replacement prosthesis of claim 1, wherein the disc member comprises in the range of two to five slits, including said first mentioned slit.

19. The implantable intervertebral disc replacement prosthesis of claim 1, wherein the disc member has two slits.

20. The implantable intervertebral disc replacement prosthesis of claim 1, the disc member further comprises a coating to promote bone fixation on at least one of the upper surface and the lower surface.

21. The implantable intervertebral disc replacement prosthesis of claim 20, wherein the coating is ceramic.

22. The implantable intervertebral disc replacement prosthesis of claim 1, wherein the disc member further comprises:

a cavity defined in the disc member about the axis;

a support ball; and an upper bearing cap and a lower bearing cap, wherein the cavity houses the support ball and is sealed by the upper bearing cap and the lower bearing cap.

23. The implantable intervertebral disc replacement of claim 1, wherein the slit is helical to the axis of the disc member.

24. The implantable intervertebral disc replacement prosthesis of claim 1, wherein:

the prosthesis comprises bearing caps to define and seal the cavity housing the support ball.

25. The implantable intervertebral disc replacement prosthesis of claim 24, wherein:

the bearing caps seal the cavity by welding, screws, pins, or by screwing into the disc member.

26. An implantable intervertebral disc replacement prosthesis, comprising:

a disc member having an upper surface, a lower surface, and a perimeter surface, and having an axis, the disc member having a slit defined in the perimeter surface to provide flexibility to the disc member, the slit having a slit thickness and terminating in a perimeter opening larger than the slit thickness, wherein each perimeter opening receives one slit, a cavity along the axis of the disc, and a support ball housed in the cavity.

27. The implantable intervertebral disc replacement prosthesis of claim 26, wherein the slit is transverse to the axis of the disc member.

28. The implantable intervertebral disc replacement prosthesis of claim 27, wherein the slit is substantially at a right angle to the axis of the disc member.

29. The implantable intervertebral disc replacement prosthesis of claim 26, wherein the perimeter opening is circular-shaped.

30. The implantable intervertebral disc replacement prosthesis of claim 26, wherein:

the prosthesis comprises bearing caps to define and seal the cavity housing the support ball.

31. The implantable intervertebral disc replacement prosthesis of claim 30, wherein:

the bearing caps seal the cavity by welding, screws, pins, or by screwing into the disc member.

* * * * *